(12) United States Patent (10) Patent No.: US 9,204,971 B2
Rydell et al. (45) Date of Patent: Dec. 8, 2015

(54) SYSTEM AND METHOD FOR ANKLE ARTHROPLASTY

(75) Inventors: Mark A. Rydell, Golden Valley, MN (US); Scott McGarvey, Edina, MN (US); Jeffrey C. Felt, Greenwood, MN (US)

(73) Assignee: MEMOMETAL TECHNOLOGIES (FR)

( * ) Notice: Subject to any disclaimer, the term of this patent is extended or adjusted under 35 U.S.C. 154(b) by 422 days.

(21) Appl. No.: 13/226,839

(22) Filed: Sep. 7, 2011

(65) Prior Publication Data

US 2011/0320005 A1 Dec. 29, 2011
US 2015/0202049 A9 Jul. 23, 2015

Related U.S. Application Data

(63) Continuation of application No. 10/562,648, filed as application No. PCT/US2004/020456 on Jun. 25, 2004, now abandoned.

(60) Provisional application No. 60/483,499, filed on Jun. 27, 2003.

(51) Int. Cl.
*A61F 2/42* (2006.01)
*A61F 2/30* (2006.01)

(52) U.S. Cl.
CPC ....... *A61F 2/4202* (2013.01); *A61F 2002/4205* (2013.01)

(58) Field of Classification Search
CPC ... A61F 2/4202; A61F 2/3872; A61F 2/4081; A61F 2/3603; A61F 2/30756; A61F 2/4684; A61F 2/4225; A61F 2/4606; A61F 2002/42; A61F 2002/4202; A61F 2002/4205; A61F 2002/4207–2002/422; A61F 2002/4261; A61F 2/4261
USPC .......... 623/21.18, 18.11, 13.12, 16.11, 21.17, 623/22.11
See application file for complete search history.

(56) References Cited

U.S. PATENT DOCUMENTS

| | | | | | |
|---|---|---|---|---|---|
| 3,140,712 | A | * | 7/1964 | Hunter | 623/18.12 |
| 3,521,302 | A | * | 7/1970 | Muller | 623/18.11 |
| 3,839,742 | A | * | 10/1974 | Link | 623/21.18 |
| 3,872,519 | A | * | 3/1975 | Giannestras et al. | 623/21.18 |
| 3,879,767 | A | * | 4/1975 | Stubstad | 623/21.19 |
| 3,889,300 | A | * | 6/1975 | Smith | 623/21.18 |
| 3,896,502 | A | * | 7/1975 | Lennox | 623/21.18 |

(Continued)

FOREIGN PATENT DOCUMENTS

FR 2803191 A1 7/2001
WO 95/30388 A1 11/1995

(Continued)

OTHER PUBLICATIONS

International Search Report, PCT/US04/20456, dated Jun. 7, 2005.

(Continued)

*Primary Examiner* — Alvin Stewart
(74) *Attorney, Agent, or Firm* — Lerner, David, Littenberg, Krumholz & Mentlik, LLP (57) ABSTRACT

A monolithic interpositional arthroplasty implant for use in repairing gyngylmus joints such as the joints of the ankle. The implant is a monolithic tibiotalar implant having a first major surface shaped to be positioned against a tibia. The tibia is allowed to articulate across the first major surface. A second major surface is shaped to be positioned against the talus.

17 Claims, 6 Drawing Sheets

(56) References Cited

U.S. PATENT DOCUMENTS

| | | | | |
|---|---|---|---|---|
| 3,896,503 | A * | 7/1975 | Freeman et al. | 623/21.18 |
| 3,975,778 | A * | 8/1976 | Newton, III | 623/21.18 |
| 3,987,500 | A * | 10/1976 | Schlein | 623/21.18 |
| D242,957 | S * | 1/1977 | Treace | D24/155 |
| 4,021,864 | A * | 5/1977 | Waugh | 623/21.18 |
| 4,069,518 | A * | 1/1978 | Groth et al. | 623/21.18 |
| 4,344,193 | A * | 8/1982 | Kenny | 623/14.12 |
| 4,385,404 | A * | 5/1983 | Sully et al. | 128/898 |
| 4,450,591 | A * | 5/1984 | Rappaport | 128/898 |
| 4,467,479 | A * | 8/1984 | Brody | 128/898 |
| 4,470,158 | A * | 9/1984 | Pappas et al. | 623/20.21 |
| 4,755,185 | A * | 7/1988 | Tarr | 623/23.4 |
| 5,171,322 | A | 12/1992 | Kenny | |
| 5,326,365 | A * | 7/1994 | Alvine | 623/21.18 |
| 5,556,429 | A | 9/1996 | Felt | |
| 5,593,445 | A * | 1/1997 | Waits | 623/23.42 |
| 5,766,259 | A * | 6/1998 | Sammarco | 623/21.18 |
| 5,782,924 | A * | 7/1998 | Johnson | 623/18.11 |
| 5,795,353 | A | 8/1998 | Felt | |
| 5,824,106 | A * | 10/1998 | Fournol | 623/21.18 |
| 5,879,387 | A * | 3/1999 | Jones et al. | 623/18.11 |
| 6,110,411 | A | 8/2000 | Clausen et al. | |
| 6,132,468 | A | 10/2000 | Mansmann | |
| 6,140,452 | A | 10/2000 | Felt et al. | |
| 6,183,519 | B1 * | 2/2001 | Bonnin et al. | 623/21.18 |
| 6,281,264 | B1 | 8/2001 | Salovey et al. | |
| 6,306,177 | B1 | 10/2001 | Felt et al. | |
| 6,436,137 | B2 | 8/2002 | Wang et al. | |
| 6,436,146 | B1 | 8/2002 | Hassler et al. | |
| 6,494,917 | B1 | 12/2002 | McKellop et al. | |
| 6,540,768 | B1 | 4/2003 | Diaz et al. | |
| 6,540,786 | B2 * | 4/2003 | Chibrac et al. | 623/18.11 |
| 6,547,828 | B2 | 4/2003 | Scott et al. | |
| 6,652,587 | B2 | 11/2003 | Felt et al. | |
| 6,673,116 | B2 | 1/2004 | Reiley | |
| 6,677,415 | B1 | 1/2004 | O'Connor et al. | |
| 6,686,437 | B2 | 2/2004 | Buchman et al. | |
| 6,726,727 | B2 | 4/2004 | Scott et al. | |
| 6,786,933 | B2 | 9/2004 | Merrill et al. | |
| 6,800,670 | B2 | 10/2004 | Shen et al. | |
| 6,814,757 | B2 * | 11/2004 | Kopylov et al. | 623/21.11 |
| 6,852,130 | B2 | 2/2005 | Keller et al. | |
| 6,866,684 | B2 * | 3/2005 | Fell et al. | 623/20.3 |
| 6,926,739 | B1 | 8/2005 | O'Connor et al. | |
| 6,966,928 | B2 * | 11/2005 | Fell et al. | 623/14.12 |
| 7,004,971 | B2 * | 2/2006 | Serhan et al. | 623/17.16 |
| 7,025,790 | B2 * | 4/2006 | Parks et al. | 623/21.18 |
| 7,037,342 | B2 * | 5/2006 | Nilsson et al. | 623/21.15 |
| 7,077,865 | B2 * | 7/2006 | Bao et al. | 623/17.12 |
| 7,166,650 | B2 | 1/2007 | Muratoglu et al. | |
| 7,244,273 | B2 * | 7/2007 | Pedersen et al. | 623/14.12 |
| 7,297,161 | B2 * | 11/2007 | Fell | 623/14.12 |
| 7,304,097 | B2 | 12/2007 | Muratoglu et al. | |
| 7,323,012 | B1 * | 1/2008 | Stone et al. | 623/21.18 |
| 7,507,774 | B2 | 3/2009 | Muratoglu et al. | |
| 7,534,270 | B2 * | 5/2009 | Ball | 623/21.18 |
| 7,569,620 | B2 | 8/2009 | Muratoglu et al. | |
| 7,611,653 | B1 * | 11/2009 | Elsner et al. | 264/255 |
| 7,635,725 | B2 | 12/2009 | Bellare et al. | |
| 7,776,097 | B2 * | 8/2010 | Tepic et al. | 623/22.24 |
| 7,796,791 | B2 * | 9/2010 | Tsougarakis et al. | 382/128 |
| 7,883,653 | B2 * | 2/2011 | Smith et al. | 264/248 |
| 7,909,882 | B2 * | 3/2011 | Stinnette | 623/23.41 |
| 7,955,393 | B2 * | 6/2011 | Hawkins | 623/20.14 |
| 7,963,996 | B2 * | 6/2011 | Saltzman et al. | 623/21.18 |
| 7,976,578 | B2 * | 7/2011 | Marvel | 623/14.12 |
| 8,002,841 | B2 * | 8/2011 | Hasselman | 623/21.18 |
| 8,003,709 | B2 | 8/2011 | Shen et al. | |
| 8,008,365 | B2 | 8/2011 | Shen et al. | |
| 8,016,884 | B2 * | 9/2011 | Shterling et al. | 623/14.12 |
| 8,076,387 | B2 | 12/2011 | Muratoglu et al. | |
| 8,092,465 | B2 * | 1/2012 | Metzger et al. | 606/96 |
| 8,100,979 | B2 * | 1/2012 | Felt et al. | 623/17.16 |
| 8,133,234 | B2 * | 3/2012 | Meridew et al. | 606/91 |
| 8,187,660 | B2 | 5/2012 | Lawrynowicz et al. | |
| 8,211,041 | B2 * | 7/2012 | Fisher et al. | 600/595 |
| 8,292,954 | B2 * | 10/2012 | Robinson et al. | 623/14.12 |
| 8,292,955 | B2 * | 10/2012 | Robinson et al. | 623/14.12 |
| 8,337,503 | B2 * | 12/2012 | Lian | 606/87 |
| 8,357,203 | B2 * | 1/2013 | White et al. | 623/21.11 |
| 8,403,985 | B2 * | 3/2013 | Hodorek | 623/14.12 |
| 8,506,637 | B2 * | 8/2013 | Schwartz | 623/17.17 |
| 8,556,971 | B2 * | 10/2013 | Lang | 623/14.12 |
| 8,568,487 | B2 * | 10/2013 | Witt et al. | 623/22.12 |
| 8,574,305 | B2 * | 11/2013 | Sanders et al. | 623/21.18 |
| 8,585,744 | B2 * | 11/2013 | Duggal et al. | 606/301 |
| 8,591,595 | B2 * | 11/2013 | Kofoed et al. | 623/21.18 |
| 8,597,361 | B2 * | 12/2013 | Sidebotham et al. | 623/18.11 |
| 8,603,180 | B2 * | 12/2013 | White et al. | 623/22.11 |
| 2001/0027345 | A1 | 10/2001 | Merrill et al. | |
| 2002/0007219 | A1 | 1/2002 | Merrill et al. | |
| 2002/0127264 | A1 | 9/2002 | Felt et al. | |
| 2002/0156531 | A1 | 10/2002 | Felt et al. | |
| 2002/0183850 | A1 | 12/2002 | Felt et al. | |
| 2002/0189622 | A1 * | 12/2002 | Cauthen et al. | 128/898 |
| 2003/0093152 | A1 * | 5/2003 | Pedersen et al. | 623/14.12 |
| 2003/0097182 | A1 | 5/2003 | Buchman et al. | |
| 2003/0181985 | A1 * | 9/2003 | Keller et al. | 623/21.18 |
| 2004/0030399 | A1 * | 2/2004 | Asencio | 623/21.18 |
| 2004/0088052 | A1 * | 5/2004 | Dearnaley | 623/16.11 |
| 2004/0092942 | A1 * | 5/2004 | Reiley | 606/87 |
| 2004/0107000 | A1 | 6/2004 | Felt et al. | |
| 2004/0117027 | A1 * | 6/2004 | Reiley | 623/21.18 |
| 2004/0133276 | A1 * | 7/2004 | Lang et al. | 623/14.12 |
| 2004/0133282 | A1 * | 7/2004 | Deffenbaugh et al. | 623/21.18 |
| 2004/0148026 | A1 * | 7/2004 | Bonutti | 623/16.11 |
| 2004/0186585 | A1 * | 9/2004 | Feiwell | 623/21.18 |
| 2004/0267277 | A1 * | 12/2004 | Zannis et al. | 606/99 |
| 2005/0004676 | A1 | 1/2005 | Schon et al. | |
| 2005/0033424 | A1 * | 2/2005 | Fell | 623/14.12 |
| 2005/0043808 | A1 * | 2/2005 | Felt et al. | 623/20.14 |
| 2005/0049710 | A1 * | 3/2005 | O'Driscoll et al. | 623/20.11 |
| 2005/0049711 | A1 * | 3/2005 | Ball | 623/21.18 |
| 2005/0146070 | A1 * | 7/2005 | Muratoglu et al. | 264/85 |
| 2005/0182492 | A1 * | 8/2005 | Pappas et al. | 623/21.18 |
| 2005/0221703 | A1 * | 10/2005 | Stone | 442/123 |
| 2005/0288792 | A1 * | 12/2005 | Landes et al. | 623/21.18 |
| 2006/0004378 | A1 * | 1/2006 | Raines et al. | 606/99 |
| 2006/0004460 | A1 * | 1/2006 | Engh et al. | 623/20.21 |
| 2006/0009853 | A1 * | 1/2006 | Justin et al. | 623/20.3 |
| 2006/0020345 | A1 * | 1/2006 | O'Connor et al. | 623/21.18 |
| 2006/0142870 | A1 * | 6/2006 | Robinson et al. | 623/21.18 |
| 2006/0149261 | A1 * | 7/2006 | Nilsson et al. | 606/72 |
| 2006/0224244 | A1 * | 10/2006 | Thomas et al. | 623/20.28 |
| 2006/0229730 | A1 * | 10/2006 | Railey et al. | 623/21.18 |
| 2006/0235517 | A1 * | 10/2006 | Hodorek | 623/14.12 |
| 2006/0241758 | A1 * | 10/2006 | Peterman et al. | 623/17.11 |
| 2006/0241778 | A1 * | 10/2006 | Ogilvie | 623/21.15 |
| 2006/0247788 | A1 * | 11/2006 | Ross | 623/21.18 |
| 2006/0293760 | A1 * | 12/2006 | DeDeyne | 623/23.76 |
| 2007/0027547 | A1 * | 2/2007 | Rydell et al. | 623/21.18 |
| 2007/0050038 | A1 * | 3/2007 | Snell et al. | 623/17.16 |
| 2007/0051180 | A1 * | 3/2007 | White | 73/760 |
| 2007/0078517 | A1 * | 4/2007 | Engh et al. | 623/20.3 |
| 2007/0100450 | A1 * | 5/2007 | Hodorek | 623/14.12 |
| 2007/0112431 | A1 * | 5/2007 | Kofoed | 623/21.18 |
| 2007/0112432 | A1 * | 5/2007 | Reiley | 623/21.18 |
| 2007/0118218 | A1 * | 5/2007 | Hooper | 623/14.12 |
| 2007/0129808 | A1 * | 6/2007 | Justin et al. | 623/20.15 |
| 2007/0173944 | A1 * | 7/2007 | Keller et al. | 623/18.11 |
| 2007/0173947 | A1 * | 7/2007 | Ratron et al. | 623/21.18 |
| 2007/0299533 | A1 * | 12/2007 | Reiley | 623/21.18 |
| 2008/0015703 | A1 * | 1/2008 | Casey | 623/17.16 |
| 2008/0046082 | A1 * | 2/2008 | Lee | 623/17.16 |
| 2008/0086210 | A1 * | 4/2008 | Fox | 623/14.12 |
| 2008/0097606 | A1 * | 4/2008 | Cragg et al. | 623/14.12 |
| 2008/0097617 | A1 * | 4/2008 | Fellinger et al. | 623/21.18 |
| 2008/0103603 | A1 * | 5/2008 | Hintermann | 623/20.32 |
| 2008/0133018 | A1 | 6/2008 | Salovey et al. | |
| 2008/0195216 | A1 * | 8/2008 | Philipp | 623/18.11 |
| 2008/0195233 | A1 * | 8/2008 | Ferrari et al. | 623/47 |
| 2008/0208346 | A1 * | 8/2008 | Schwartz | 623/17.17 |
| 2008/0234820 | A1 * | 9/2008 | Felt et al. | 623/14.12 |
| 2009/0048687 | A1 * | 2/2009 | Tornier et al. | 623/47 |

(56) References Cited

U.S. PATENT DOCUMENTS

| | | | |
|---|---|---|---|
| 2009/0054992 A1* | 2/2009 | Landes et al. | 623/21.18 |
| 2009/0082875 A1* | 3/2009 | Long | 623/21.18 |
| 2009/0088846 A1* | 4/2009 | Myung et al. | 623/14.12 |
| 2009/0118830 A1* | 5/2009 | Fell | 623/14.12 |
| 2009/0138096 A1* | 5/2009 | Myerson et al. | 623/54 |
| 2009/0182377 A1* | 7/2009 | Petersen | 606/247 |
| 2009/0182433 A1* | 7/2009 | Reiley et al. | 623/18.11 |
| 2009/0187252 A1* | 7/2009 | Howald et al. | 623/22.15 |
| 2009/0198341 A1* | 8/2009 | Choi et al. | 623/21.18 |
| 2009/0226068 A1* | 9/2009 | Fitz et al. | 382/131 |
| 2009/0240338 A1* | 9/2009 | Reiley | 623/21.18 |
| 2009/0259314 A1* | 10/2009 | Linder-Ganz et al. | 623/14.12 |
| 2009/0306778 A1* | 12/2009 | Marvel | 623/14.12 |
| 2009/0317767 A1 | 12/2009 | Burger et al. | |
| 2009/0326659 A1 | 12/2009 | Muratoglu et al. | |
| 2010/0057215 A1* | 3/2010 | Graham | 623/21.15 |
| 2010/0057216 A1* | 3/2010 | Gannoe et al. | 623/21.18 |
| 2010/0168859 A1* | 7/2010 | Wardlaw | 623/17.12 |
| 2010/0174376 A1* | 7/2010 | Lang | 623/18.11 |
| 2010/0198355 A1* | 8/2010 | Kofoed et al. | 623/21.18 |
| 2010/0204799 A1* | 8/2010 | Keller et al. | 623/18.11 |
| 2010/0262251 A1 | 10/2010 | Muratoglu et al. | |
| 2010/0298945 A1 | 11/2010 | Schroeder et al. | |
| 2010/0312348 A1 | 12/2010 | Wang et al. | |
| 2010/0312353 A1* | 12/2010 | Howald et al. | 623/23.12 |
| 2010/0318088 A1* | 12/2010 | Warne et al. | 606/87 |
| 2011/0004305 A1* | 1/2011 | Jansson et al. | 623/14.12 |
| 2011/0004315 A1 | 1/2011 | Muratoglu et al. | |
| 2011/0022089 A1* | 1/2011 | Assell et al. | 606/247 |
| 2011/0029094 A1* | 2/2011 | Hogendijk et al. | 623/21.12 |
| 2011/0035012 A1* | 2/2011 | Linares | 623/18.11 |
| 2011/0035019 A1 | 2/2011 | Goswami et al. | |
| 2011/0060366 A1* | 3/2011 | Heim et al. | 606/247 |
| 2011/0066243 A1* | 3/2011 | Rivin et al. | 623/14.12 |
| 2011/0093073 A1* | 4/2011 | Gatt et al. | 623/14.12 |
| 2011/0098746 A1* | 4/2011 | Peterson et al. | 606/249 |
| 2011/0098816 A1* | 4/2011 | Jacob et al. | 623/17.11 |
| 2011/0144757 A1* | 6/2011 | Linares | 623/18.11 |
| 2011/0208317 A1* | 8/2011 | Feldman | 623/21.18 |
| 2011/0257753 A1 | 10/2011 | Gordon et al. | |
| 2011/0272862 A1 | 11/2011 | Schroeder et al. | |
| 2011/0288642 A1* | 11/2011 | Forsell | 623/14.12 |
| 2011/0288643 A1* | 11/2011 | Linder-Ganz et al. | 623/14.12 |
| 2011/0320005 A1* | 12/2011 | Rydell et al. | 623/21.18 |
| 2012/0004734 A1 | 1/2012 | Reiley | |
| 2012/0010718 A1 | 1/2012 | Still | |
| 2012/0010719 A1 | 1/2012 | Reiley | |
| 2012/0046753 A1 | 2/2012 | Cook et al. | |
| 2012/0089232 A1 | 4/2012 | Choi et al. | |
| 2012/0109334 A1* | 5/2012 | Forsell | 623/23.14 |
| 2012/0116531 A1* | 5/2012 | Forsell | 623/23.11 |
| 2012/0185050 A1* | 7/2012 | Schwartz | 623/17.17 |
| 2012/0191211 A1 | 7/2012 | Drozd | |
| 2012/0209382 A1* | 8/2012 | Forsell | 623/14.12 |
| 2012/0232575 A1* | 9/2012 | Wirtel et al. | 606/192 |
| 2012/0232657 A1* | 9/2012 | Myung et al. | 623/14.12 |
| 2012/0245701 A1* | 9/2012 | Zak et al. | 623/21.18 |
| 2012/0310244 A1* | 12/2012 | Blain et al. | 606/79 |
| 2012/0316645 A1* | 12/2012 | Grotz | 623/14.13 |
| 2013/0030542 A1* | 1/2013 | Grotz | 623/20.35 |
| 2013/0073050 A1 | 3/2013 | McEntire et al. | |
| 2013/0144389 A1* | 6/2013 | Bonutti | 623/17.16 |
| 2013/0158658 A1* | 6/2013 | Hayzlett | 623/8 |
| 2013/0204386 A1* | 8/2013 | Sanders et al. | 623/21.18 |
| 2013/0245773 A1 | 9/2013 | Muratoglu et al. | |
| 2013/0245803 A1* | 9/2013 | Lang | 700/98 |
| 2013/0297034 A1* | 11/2013 | Reiley | 623/21.18 |
| 2013/0304224 A1* | 11/2013 | Schmidt et al. | 623/21.18 |
| 2013/0310943 A1* | 11/2013 | McCormack et al. | 623/17.16 |
| 2013/0325009 A1* | 12/2013 | Duggal et al. | 606/64 |
| 2014/0018925 A1* | 1/2014 | Schwartz | 623/17.17 |
| 2014/0018931 A1* | 1/2014 | Gillard et al. | 623/21.18 |
| 2014/0046450 A1* | 2/2014 | Kellar et al. | 623/18.11 |
| 2014/0074245 A1* | 3/2014 | Shohat et al. | 623/19.13 |

FOREIGN PATENT DOCUMENTS

| | | |
|---|---|---|
| WO | 98/20939 A2 | 5/1998 |
| WO | 02/17821 A2 | 3/2002 |
| WO | 03/053278 A2 | 7/2003 |
| WO | 03/061522 A2 | 7/2003 |
| WO | 2004/006811 A2 | 1/2004 |

OTHER PUBLICATIONS

Brown, Roger, Handbook of Polymer Testing: Physical Methods, CRC Press, 1999, ISBN: 978-0824701710.

* cited by examiner

SYSTEM AND METHOD FOR ANKLE ARTHROPLASTY

CROSS REFERENCE TO RELATED APPLICATIONS

The present application is a continuation of U.S. patent application Ser. No. 10/562,648 filed May 2, 2006, now abandoned, which is a national phase entry under 35 U.S.C. §371 of International Application No. PCT/US2004/020456 filed Jun. 25, 2004, which claims priority from U.S. Provisional Patent Application No. 60/483,499 filed Jun. 27, 2003.

TECHNICAL FIELD

In one aspect, this invention relates to biomaterials for implantation and use within the body. In yet another aspect, this invention further relates to the field of orthopedic implants and prostheses, and more particularly, for implantable materials for use in orthopedic joints.

BACKGROUND OF THE INVENTION

Applicant has previously described, inter alia, prosthetic implants formed of biomaterials that can be delivered and finally cured in situ, and/or that can be partially or fully prepared ex vivo, for implantation into the body, e.g., using minimally invasive techniques. See for instance, U.S. Pat. Nos. 5,556,429; 5,795,353; 6,140,452; 6,306,177; and 6,652,587, as well as US Application Publication Nos. US-2002-0156531; US-2002-0127264; US-2002-0183850; and US-2004-0107000, and International applications having Publication Nos. WO 95/30388; WO 98/20939; WO 02/17821; WO 03/053278; WO 03/061522, and WO 2004/006811 (the disclosures of each of which are incorporated herein by reference).

In spite of developments to date, there remains a need for a joint prosthesis system that provides an optimal combination of properties such as ease of preparation and use, and performance within the body, and particularly for use in joints other than the knee.

SUMMARY OF THE INVENTION

The present invention provides an interpositional arthroplasty system for use in repairing ginglymus joints such as the joints of the ankle. In some preferred embodiments, the system includes an implant designed to be positioned in the tibiotalar (true ankle joint) and/or in the subtalar joint. The implant can comprise one or more biomaterials such as polymers, ceramics, and/or metals, including combinations thereof.

In a preferred embodiment, the invention provides a tibiotalar implant that provides a first major surface adapted to be positioned against a tibia and a second major surface adapted to be positioned against a talus. In a further preferred embodiment, the implant includes one or more structures adapted to improve retention of the implant within the joint site, e.g., by means of an integral bead shaped structure proximate its anterior side adapted to cap and thereby engage the neck of the talus.

In other preferred embodiments, the invention provides a polymeric ankle implant that provides a first major surface adapted to be positioned against a talus and a second major surface adapted to be positioned against the calcaneus bone. In a further embodiment, the implant includes one or more structures adapted to improve retention of the implant within the joint site, e.g. by a shape that conforms to the calcaneus, posterior lip, and/or anterior lip. Such an implant can be useful for correcting various deformities of an ankle, such as creating space between bones in the foot to reduce bone on bone impingement, as well as increasing articulation of a joint.

Some embodiments of the system can also include one or more components and one or more related devices, in the form of a kit that can be used to provide or perform some or all of the steps of preparing the joint to receive an implant, determining an appropriate implant size for a particular joint, determining an appropriate implant thickness and/or angle, inserting the implant into the joint, and/or seeming the implant to a desired extent. One or more of the various components and devices, including optionally one or more implants themselves, can be provided or packaged separately or in varying desired combinations and subcombinations to provide a kit of this invention. Further, the invention also includes a method of repairing a ginglymus joint, as well as a ginglymus joint that includes an implant of this invention.

In preferred embodiments, the invention provides a prosthetic device for implantation into an ankle joint space within the body of a mammal, the device comprising a composite or monolith structure fabricated from a biocompatible, biodurable material that is adapted to be inserted into the joint compartment. More preferably, the implanted device is substantially free of anchoring portions that need to be attached to the bone, cartilage, ligaments or other tissue, yet by its design is capable of being used with minimal translation, rotation, or other undesired movement or dislocation within or from the joint space. The stability of the device within the joint space is provided, in whole or in part, by the fixation/congruency of the device to the one or the other, and generally the relatively less mobile, of the two joint members.

BRIEF DESCRIPTION OF THE DRAWING

FIG. 2(*a*) is a top view of a tool useful for preparing a joint to receive an implant in accordance with an embodiment of the present invention.

FIG. 2(*b*) is a side view of a tool useful for preparing a joint to receive an implant in accordance with an embodiment of the present invention.

FIG. 2(*c*) is a bottom view of a tool useful for preparing a joint to receive an implant in accordance with an embodiment of the present invention.

FIG. 3(*a*) is a top view of a sizing tool in accordance with an embodiment of the present invention.

FIG. 3(*b*) is a side view of a sizing tool in accordance with an embodiment of the present invention.

FIG. 4(*a*) is a top view of a gripping tool in accordance with an embodiment of the present invention.

FIG. 4(*b*) is a side view of a gripping tool in accordance with an embodiment of the present invention.

FIG. 4(*c*) is a side view of a gripping tool in accordance with an alternate embodiment of the present invention.

FIG. 6(*a*) is a side view of an implant in accordance with an embodiment of the present invention.

FIG. 6(*b*) is a top view of an implant in accordance with an embodiment of the present invention.

DETAILED DESCRIPTION

Figure 1:
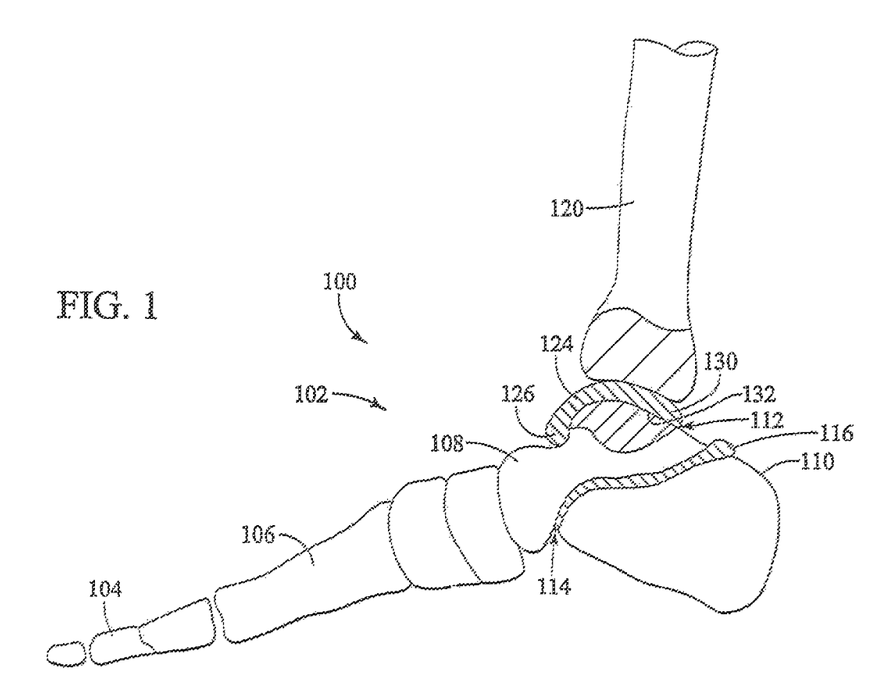
FIG. 1 is a side view of a foot and ankle region showing implants in accordance with an embodiment of the present invention.

A preferred embodiment will be described with reference to the figures, where FIG. 1 is a side view of a foot 100 including a plurality of bones 102. The bones of foot 100 include a first phalanges 104, a metatarsal bone 106, a talus 108, and calcaneus 110. A tibia 120 is also shown in FIG. 1. As shown in FIG. 1, the tibia 120 and talus 108 form a tibiotalar joint 112 (sometimes referred to as a true ankle joint or TAJ). The tibiotalar joint 112 is responsible for up and down motion of the foot. The talus 108 and calcaneus 110 form a subtalar joint 114. The subtalar joint 114 allows for side to side motion of the foot.

In the embodiment of FIG. 1 a tibiotalus implant 124 is disposed between tibia 120 and talus 108. The tibiotalus implant 124 can be useful for treating arthritic joints, replacing natural cartilage, and/or providing a separation between the tibia 120 and talus 108 to reduce bone on bone contact during articulation. The tibiotalus implant 124 can have a first major surface 130 useful for positioning against the tibia 120. The first surface 130 can be adapted to provide an articulating surface for articulation of the tibia 120. The tibiotalus implant can also have a second major surface 132 adapted for positioning against the talus 108. The second surface 132 can be useful for providing a cushioning surface and/or congruency with the talus 108. In such embodiments, the tibiotalar implant 124 can be adapted to provide a combination of desirable wear resistance, congruency, and cushioning properties.

The tibiotalus implant 124 can be provided with means for stabilizing (e.g., fixing) the implant 124 within the joint, wherein the means for stabilizing provides for less motion of the implant relative to the talus 108 than the tibia 120. With reference to FIG. 1, it will be appreciated that an exemplary means for stabilization means includes a tibiotalus implant 124 that has a bead shaped structure 126 proximate its anterior side that engages the neck of the talus 108 to reduce the likelihood of anterior and posterior movement during articulation. Of course, other stabilization means can be provided to relatively fix the tibiotalar implant 124 to the talus 108.

The implant 124 can comprise any shape or size that is therapeutically useful. In some embodiments, the implant 124 may be between about 1 mm and 7 mm thick. In a preferred embodiment, the implant 124 is between about 2 mm and 3 mm thick. The implant 124 can also be sized to substantially cover the surface of the top portion of the talus 108. In such embodiments, the implant 124 can be about 40 mm to 50 mm in length.

Figure 6:
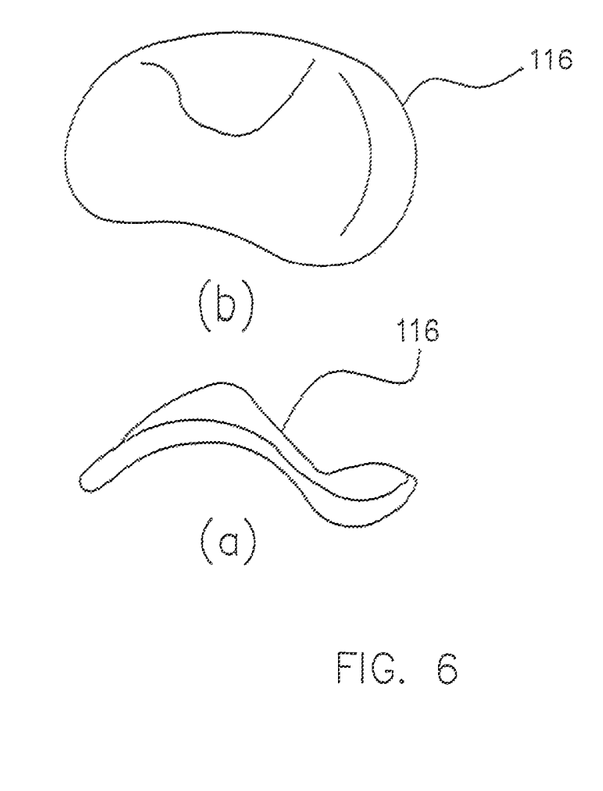

Also in the embodiment of FIG. 1, a second implant 116 is disposed between talus 108 and calcaneus 120. In some embodiments, talus-calcaneus implant 116 can be relatively fixed to calcaneus 110 and allow talus 108 to articulate against it. As shown in FIGS. 6(a) and (b) implant 116 can contain an S-shaped side cross-section useful for following the contour of the calcaneus 110. Further, implant 116 can contain a posterior lip and/or a anterior lip, each of which are useful for engaging the calcaneus 120 to increase stabilization.

The implant 116 can comprise any shape or size that is therapeutically useful. In some embodiments, implant 116 is between about 2 mm and 5 mm thick. In some preferred embodiments, implant 116 is between about 2.5 mm and 3.5 mm thick. Implant 116 can be sized to substantially cover the top surface of the calcaneus 120. For example, the implant 116 can be about 35 mm to 45 mm in length.

Some embodiments of the system can also include one or more devices in the form of a kit that can be used to provide or perform some or all of the steps of preparing the joint to receive an implant, determining an appropriate implant size for a particular joint, determining an appropriate implant thickness and/or angle, inserting the implant into the joint, and/or securing the implant to a desired extent. One or more of the various components and devices, including optionally one or more implants themselves, can be provided or packaged separately or in varying desired combinations and sub-combinations to provide a kit of this invention.

Figures 2A, 2B:
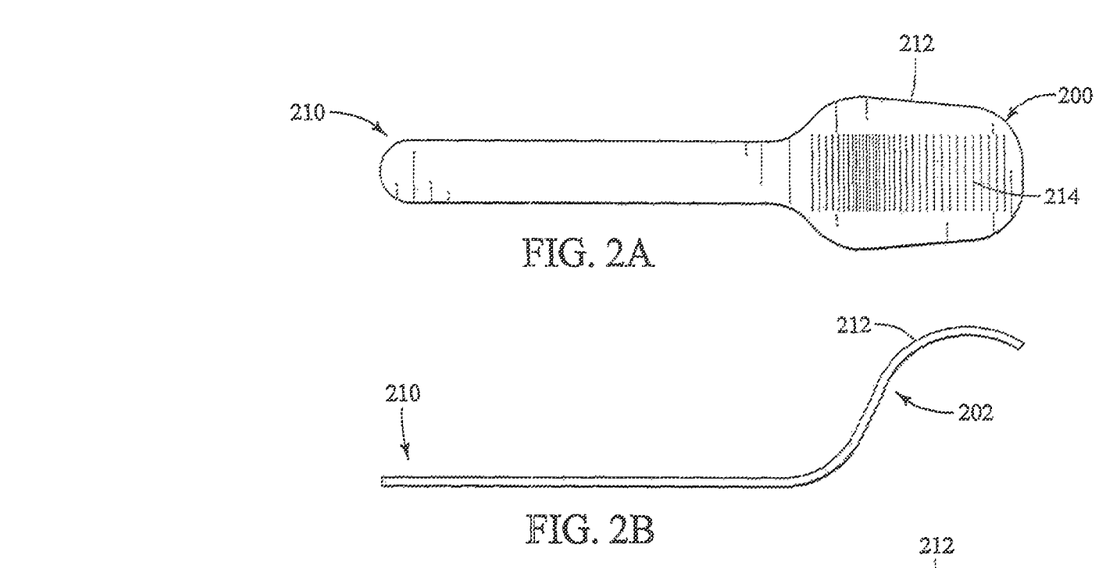
Figure 2C:
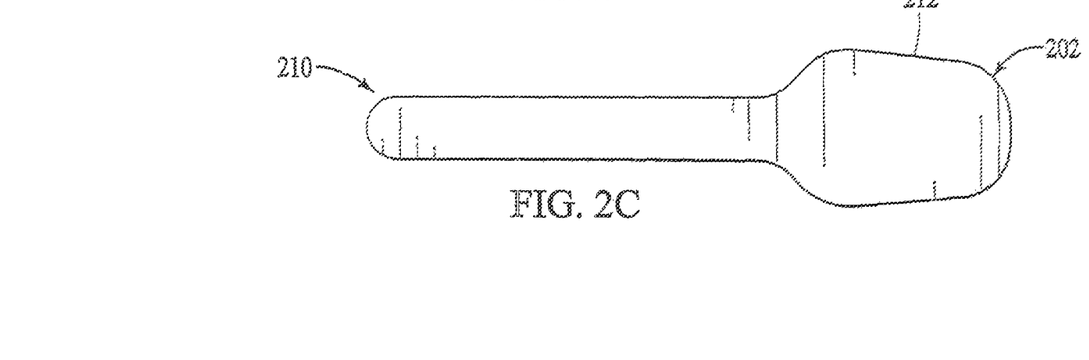

In some embodiments, at least one tool is provided for preparing the joint to receive an implant. Such a tool can comprise a tibial smoother 200 and/or a talus smoother 202 as shown in FIGS. 2(a)-(c). Both the tibial smoother 200 and the talus smoother 202 can be provided with a proximate end 210 useful for manual or motorized manipulation and a smoothing end 212 useful for smoothing the surface of a bone. The smoothing end 212 can be provided with any structure or feature that allows it to adequately remove osteophytes, cartilage and other deposits to smooth the surface, of a bone, such as grit portion 214. In some embodiments, smoothing end 212 is fenestrated. Such embodiments are useful for smoothing the tibia and talus simultaneously, as well as for providing self-cleaning properties by allowing debris to pass between the superior and anterior sides. Grit portion 214 can be relatively courser for removing larger osteophytes or can be relatively finer for smoothing small osteophytes and finer finishing of the bone surface. Smoother 200 can also be universal in its orientation, permitting it to be used smoothing bone in both the right and left ankles.

Figure 3A:
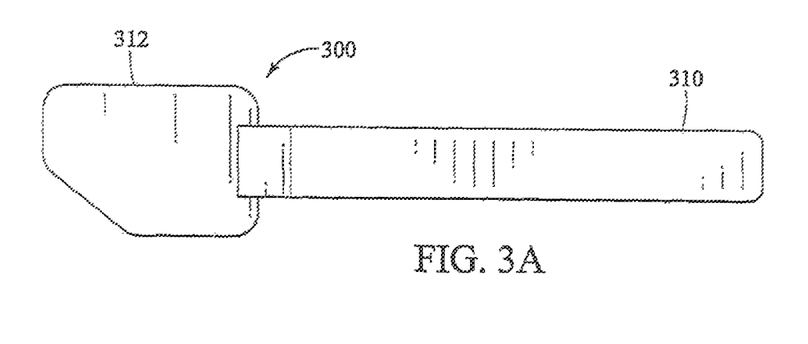
Figure 3B:
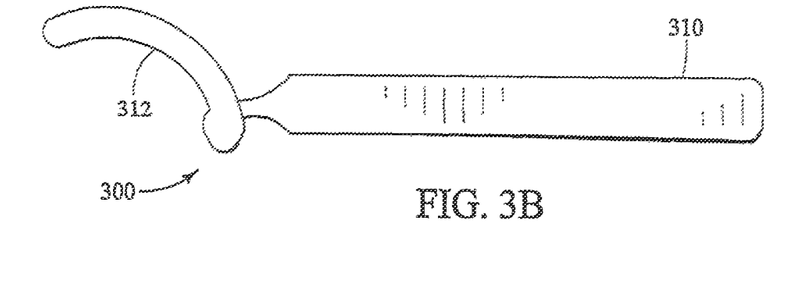

In some embodiments, at least one sizing tool for determining an appropriate implant thickness and/or angle is provided. Such a tool can comprise an implant sizer 300 as shown in FIGS. 3(a) and (b). Sizing tool 300 can include proximate end 310 useful for manual manipulation and a sizing end 312 useful for inserting into the body to determine an appropriate implant size. As shown in FIGS. 3(a) and (b), the sizing end 312 can be shaped substantially as an implant. One or more sizing tools 300 can be provided in the form of a kit, with each tool 300 having an identifiable shape, thickness, or angle. In some embodiments, sizing tool 300 is provided with means for adjusting its thickness, such as a track with one or more components that can be locked in to increase thickness.

Figure 4A:
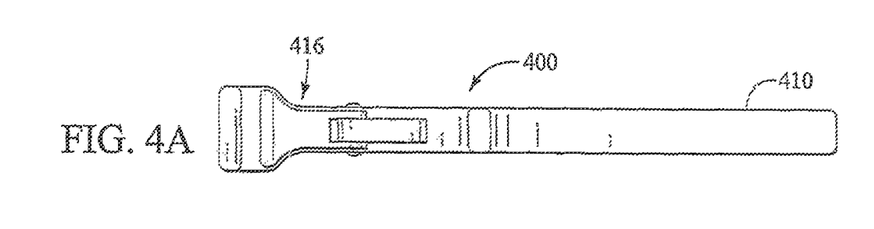
Figure 4B:
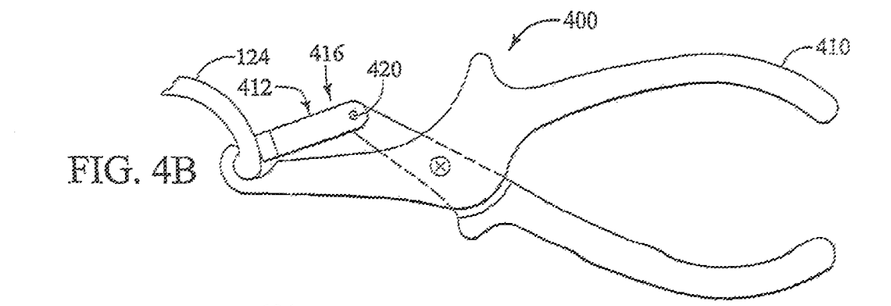
Figure 4C:
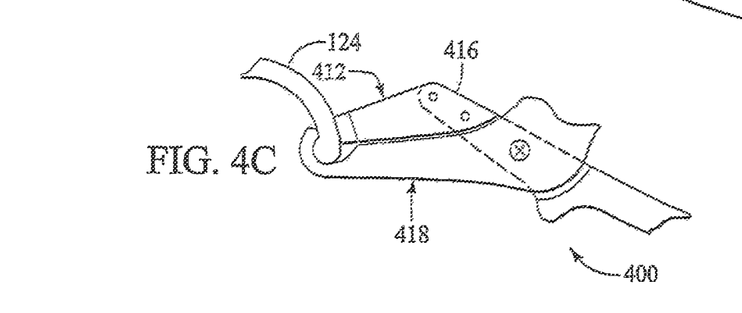

In some embodiments, a tool is provided for inserting an implant into a joint and or securing the implant to a desired extent. Such a tool can comprise an implant gripper 400 as shown in FIGS. 4(a)-(c). Gripper 400 can be provided with a proximate end 410 useful for manual manipulation and an gripping end 412 useful for gripping and retaining an implant 124 for placement into a body. Gripping end 412 can include a top arm 416 and a bottom arm 418 useful for gripping and retaining an implant 124. As shown in FIG. 4(b), top arm 416 can include a hinge 420 useful for providing top arm 416 with a lower profile when releasing implant 124. Other embodiments, such as the one shown in FIG. 4(c), do not include a hinge 420.

Figure 5:
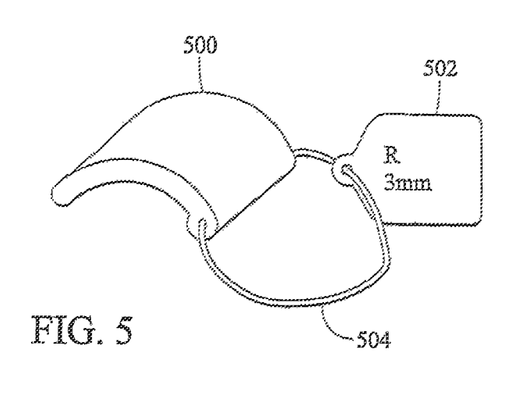
FIG. 5 is a perspective view of an implant template in accordance with an embodiment of the present invention.

The present invention can also include one or more implant templates 500, as shown in FIG. 5. Implant template 500 is useful for determining the proper implant thickness and/or angle need to match physiological values. Implant template 500 may be provided in a variety of thicknesses and shapes, e.g. shapes useful for the right and left ankles. A marker, such as a dog tag 502, can be provided to list this information. In some embodiments, implant template 500 can be inserted with gripper 400. A band, e.g. a chain 504 can be provided to remove the implant template 500 from the joint. In some embodiments, chain 504 can also retain dog tag 502. Of course, the implant itself may be provided with a marker, such as a dog tag 502 and a band 504, which can be removed at the time of implantation.

The tools described above can be constructed of any suitable material. For example, the tools can be constructed of stainless steel, ceramic, and/or polymeric materials. Embodiments constructed at least partially of stainless steel can be relatively more suitable for providing a reusable tool, and embodiments constructed at least partially of a polymer can be relatively more suitable for providing a disposable tool. Further, all of the tools above can be shaped to provide an ergonomic fit for the user. Some embodiments provide a universal tool that can be adapted, e.g., configured, to provide an ergonomic fit for both left and right hands.

In one exemplary ankle surgery method in accordance with the present invention, an incision is made in the front of the foot, anterior to the tibiotalar joint 112. The tibiotalar implant 124 is inserted into the space between the two bones. In embodiments provided with a bead shaped structure 126, the head shaped structure 126 is placed in contact with the neck of the talus 108 to reduce the likelihood of anterior and posterior movement during articulation. The implant can be further restrained by adjacent soft tissue. The incision is finally sutured closed.

In one exemplary ankle surgery method in accordance with the present invention, an incision is made in the lateral side of the foot. The subtalar implant 116 is inserted into the space between the talus 108 and the calcaneus 110. In embodiments provided with a posterior and/or anterior lip, such lip is placed in contact with the calcaneus 110 to reduce the likelihood of anterior and posterior movement during articulation. The implant can be further restrained by adjacent soft tissue. The incision is finally sutured closed.

The methods of repairing the joints described above can also include the steps of preparing a joint to receive an implant, determining an appropriate implant size for a particular joint, determining an appropriate implant thickness, inserting the implant into the joint, and/or securing the implant to a desired extent. In some embodiments, these steps are performed with the use of one or more of the tools or apparatus described above.

In some embodiments, implants 124 and 116 may be provided with means to confirm their post-operative position. For example, implants 124 and 116 can be radio-opaque. In such embodiments, a radio-opaque material, such as tungsten, can be provided within the implant in one or more locations. The implant location can then be determined using radio-opacity techniques known in the art.

The biomaterial earl be prepared from any suitable material. Generally, a material is suitable if it has appropriate biostability, biodurability and biocompatibility characteristics. Typically, the materials include polymeric materials, having an optimal combination of such properties as biostability, biocompatibility, physical strength and durability, and compatibility with other components (and/or biomaterials) used in the assembly of a final composite.

Examples of polymeric materials that may be suitable in some applications, either alone or in combination, include polyurethane, available from Polymer Technology Group Incorporated under the names Bionate,™ Biospan,™ and Blasthane™, available from Dow Chemical Company under the name Pellethane,™ and available from Bayer Corp. under the names Bayflex,™ Texin,™ and Desniopan;™ ABS, available from GE Plastics under the name Cyclolac™, and available from Dow Chemical Company under the name Magrunn;™ SAN, available from Bayer Plastics under the name Lustran;™ Acetal, available from Dupont under the name Delrin,™ and available from Ticona GmbH and/or Ticona LLC (Ticona) under the name Celcon;™ polycarbonate, available from GE Plastics under the name Lexan,™ and available from Bayer Corp. under the name Makrolon;™ polyethylene, available from Huntsman LLC, and available from Ticona under the names GUR 1020™ and GUR 1050;™ polypropylenes, available from Solvay Engineered. Polymers, Inc. under the name Dexflex;™ aromatic polyesters, available from Ticona; polyetherimide (PE), and available from GE Plastics under the name Ultem;™ polyamideimide (PAI), available from DSM E Products under the name Torlon;™ polyphenylene sulfide, available from Chevron Phillips Chemical Company LP under the name Ryton;™ polyester, available from Dupont under the name Dacron;™ polyester thermoset, available from Ashland Specialty Chemical Company under the name Aropol;™ polyureas; hydrogels, available from Hydromer Inc.; liquid crystal polymer, available from Ticona under the name Vectra;™ polysiloxanes, available from Nusil Technologies, Inc.; polyacrylates, available from Rohm & Haas under the name Plexiglas;™ epoxies, available from Ciba Specialty Chemicals; polyimides, available from Dupont under the names Kapton,™ and Vespel;™ polysulfones, available from BP Amoco Chemicals under the name Udel,™ and available from BASF Corporation under the name Ultrason;™ PEAK/PEEK, available from Victrex under the name Victrex PEAK;™ as well as biopolymers, such as collagen or collagen-based materials, chitosan and similar polysaccharides, and combinations thereof. Of course, any of the materials suitable for use in a composite or single biomaterial implant may be structurally enhanced with fillers, fibers, meshes or other structurally enhancing means.

The present provides a biomaterial having an improved combination of properties for the preparation, storage, implantation and long terra use of medical implants. The improved properties correspond well for the preparation and use of an implant having both weight bearing and/or articulating functions, and preferably in the form of an implant for interpositional arthroplasty.

In turn, a preferred biomaterial of this invention provides an optimal combination of properties relating to wear resistance, congruence, and cushioning while meeting or exceeding requirements for biocompatibility, all in a manner that serves to reduce the coefficient of friction at the major motion interface.

Wear resistance can be assessed by determining parameters such as DIN abrasion and flexural stress strain fatigue resistance. A preferred implant will have sufficient wear resistance to avoid the generation of clinically significant particulate debris over the course of the implant's use.

Congruence can be assessed by determining parameters such as tensile modulus compressive modulus, and hardness, to determine the manner and extent to which the implant will conform itself to possible other components of the implant itself and/or to bone or surrounding tissue.

Cushioning can be assessed by determining such parameters as hardness, compressive modulus, and tensile modulus, to determine the elastomeric nature of the material, and in turn, its suitability for use in a weight bearing joint. More elastomeric materials will generally provide greater comfort in weight bearing applications, particularly if the other physical properties can be maintained.

Applicant has discovered that improved wear resistance, congruence, and/or cushioning toughness can be achieved without undue effect on other desired properties, such as abrasion, hardness, specific gravity, tear resistance, tensile strength, ultimate elongation, and biocompatibility. Moreover, Applicant has discovered that such properties can themselves be provided in varying forms, as between first and second biomaterials of a composite of the present invention.

A polymeric biomaterial of this invention can be prepared using any suitable means, including by curing the polymer ex vivo. The composition can be used in any suitable combination with other materials, including other compositions of the same or similar nature, as well as other materials such as natural or synthetic polymers, metals, ceramics, and the like.

The invention further provides a method of preparing the composition, a method of using the composition, implants that comprise the composition, as well as methods of preparing and using such implants.

The biomaterial used in this invention preferably includes polyurethane components that are reacted ex vivo to form a polyurethane ("PU"). The formed PU, in turn, includes both hard and soft segments. The hard segments are typically comprised of stiffer oligourethane units formed from diisocyanate and chain extender, while the soft segments are typically comprised of one or more flexible polyol units. These two types of segments will generally phase separate to form hard and soft segment domains, since they tend to be incompatible with one another. Those skilled in the relevant art, given the present teaching, will appreciate the manner in which the relative amounts of the hard and soft segments in the formed polyurethane, as well as the degree of phase segregation, can have a significant impact on the final physical and mechanical properties of the polymer. Those skilled in the art will, in turn, appreciate the manner in which such polymer compositions can be manipulated to produce cured and curing polymers with desired combination of properties within the scope of this invention.

The hard segments of the polymer can be formed by a reaction between the diisocyanate or multifunctional isocyanate and chain extender. Some examples of suitable isocyanates for preparation of the hard segment of this invention include aromatic diisocyanates and their polymeric form or mixtures of isomers or combinations thereof, such as toluene diisocyanates, naphthalene diisocyanates, phenylene diisocyanates, xylylene diisocyanates, and diphenylmethane diisocyanates, and other aromatic polyisocyanates known in the art. Other examples of suitable polyisocyanates for preparation of the hard segment of this invention include aliphatic and cycloaliphatic isocyanates and their polymers or mixtures or combinations thereof, such as cyclohexane diisocyanates, cyclohexyl-bis methylene diisocyanates, isophorone diisocyanates and hexamethylene diisocyanates and other aliphatic polyisocyanates. Combinations of aromatic and aliphatic or arylakyl diisocyanates can also be used.

The isocyanate component can be provided in any suitable form, examples of which include 2,4'-diphenylmethane diisocyanate, 4,4'-diphenylmethane diisocyanate, and mixtures or combinations of these isomers, optionally together with small quantities of 2,2'-diphenylmethane diisocyanate (typical of commercially available diphenylmethane diisocyanates). Other examples include aromatic polyisocyanates and their mixtures or combinations, such as are derived from phosgenation of the condensation product of aniline and formaldehyde. It is suitable to use an isocyanate that has low volatility, such as diphenylmethane diisocyanate, rather than more volatile materials such as toluene diisocyanate. An example of a particularly suitable isocyanate component is the 4,4'-diphenylmethane diisocyanate ("MDI"). Alternatively, it can be provided in liquid form as a combination of 2,2'-, 2,4'- and 4,4'-isomers of MDI. In a preferred embodiment, the isocyanate is MDI and even more preferably 4,4'-diphenylmethane diisocyanate.

In one embodiment of the invention, the isocyanate is 4,4'-diphenylmethane, diisocyanate (as available from Bayer under the tradename Mondur M), from preferably about 20 to 60 weight percent, more preferably from about 30 to 50 weight percent. The actual amount of isocyanate used should be considered in combination with other ingredients and processing parameters, particularly including the amount of chain extender (such as butanediol (BDO)) used, since the combination typically determines the hard segment component, and in turn hardness, of the corresponding cured polymer. Hardness correlates in a generally proportional fashion with the combined weights of MDI and BDO, such that compositions having between 30 and 60 total weight percent (MDI+BDO) are generally useful, with those compositions having between about 50 to about 60 total weight percent being somewhat harder, and particularly useful for either the first (femoral contacting) biomaterial and surface of a composite implant or for implants having a single biomaterial providing both first and second surfaces. By contrast, compositions having between about 40 to about 50 total weight percent are somewhat more congruent and cushioning, though less wear resistant, and therefore are preferred for use as the second biomaterial, e.g., tibial contacting surface, of a composite implant as described herein.

Some examples of chain extenders for preparation of the hard segment of this invention include, but are not limited, to short chain diols or triols and their mixtures or combinations thereof, such as 1,4-butane diol, 2-methyl-1,3-propane diol, 1,3-propane-diol ethylene glycol, diethylene glycol, glycerol, tri-methylpropane, cyclohexane dimethanol, triethanol amine, and methyldiethanol amine. Other examples of chain extenders for preparation of the hard segment of this invention include, but are not limited to, short chain diamines and their mixtures or combinations thereof, such as dianiline, toluene diamine, cyclohexyl diamine, and other short chain diamines known in the art.

The soft segment consists of urethane terminated polyol moieties, which are formed by a reaction between the polyisocyanate or diisocyanate or polymeric diisocyanate and polyol. Examples of suitable diisocyanates are denoted above. Some examples of polyols for preparation of the soft segment of this invention include but are not limited to polyalkylene oxide ethers derived form the condensation of alkylene oxides (e.g. ethylene oxide, propylene oxide, and blends thereof), as well as tetrahyrofuran based polytetramethylene ether glycols, polycaprolactone diols, polycarbonate diols and polyester diols and combinations thereof. In a preferred embodiment, the polyols are polytetrahydrofuran polyols ("PTHF"), also known as polytetramethylene oxide ("PTMO") or polytetramethylene ether glycols ("PTMEG"). Even more preferably, the use of two or more of PTMO diols with different molecular weights selected from the commercially available group consisting of 250, 650, 1000, 1400, 1800, 2000 and 2900.

Two or more PTMO diols of different molecular weight can be used as a blend or separately, and in an independent fashion as between the different parts of a two part system. The solidification temperature(s) of PTMO diols is generally proportional to their molecular weights. The compatibility of the PTMO diols with such chain extenders as 1,4-butanediol is generally in the reverse proportion to the molecular weight of the diol(s). Therefore the incorporation of the low molecular weight PTMO diols in a "curative" (part B) component of a two part system, and higher molecular weight PTMO diols in the prepolymer (part A) component, can provide a two-part system that can be used at relatively low temperature. In turn, good compatibility of the low molecular weight PTMO diols with such chain extenders as 1,4-butanediol permits the preparation of two part systems with higher (prepolymer to curative) volume ratio. Amine terminated polyethers and/or polycarbonate-based diols can also be used for building of the soft segment.

In one embodiment of the invention, the polyol is polytetramethyleneetherglycol 1000 (as available from E.I. du Pont de Nemours and Co. under the tradename Terathane 1000), preferably from about 0 to 40 weight percent, more preferably from about 10 to 30 weight percent, and perhaps even more preferably from about 22 to 24 weight percent, based on the total weight of the polymer. The polyol disclosed above may be used in combination with polytetramethyleneethenglycol 2000 (as available from E.I. du Pont de Nemours and Co. under the tradename Terathane 2000), preferably from about 0 to 40 weight percent, more preferably from about 10 to 30 weight percent, and perhaps even more preferably from about 17 to 18 weight percent, based on the total weight of the polymer.

In one embodiment, the biomaterial may include a chain extender. For example, the chain extender may be 1,4-butanediol (as available from Sigma Aldrich Corp.), preferably from about 1 to 20 weight percent, more preferably from 5 to 15 weight percent, to perhaps even more preferably from 12 to 13 weight percent, based on the total weight of the polymer.

The polyurethane can be chemically crosslinked, e.g., by the addition of multifunctional or branched OH-terminated crosslinking agents or chain extenders, or multifunctional isocyanates. Some examples of suitable crosslinking agents include, but are not limited to, trimethylol propane ("TMP"), glycerol, hydroxyl terminated polybutadienes, hydroxyl terminated polybutadienes (HOPB), trimer alcohols, Castor oil polyethyleneoxide (PEO), polypropyleneoxide (PPO) and PEO-PPO triols. In a preferred embodiment, HOPB is used as the crosslinking agent.

This chemical crosslinking augments the physical or "virtual" crosslinking of the polymer by hard segment domains that are in the glassy state at the temperature of the application. The optimal level of chemical cross-linking improves the compression set of the material, reduces the amount of the extractable components, and improves the biodurability of the PU. This can be particularly useful in relatively soft polyurethanes, such as those suitable for the repair of damaged cartilage. Reinforcement by virtual cross-links alone may not generate sufficient strength for in vivo performance in certain applications. Additional cross-linking from the soft segment, potentially generated by the use of higher functional polyols can be used to provide stiffer and less elastomeric materials. In this manner a balancing of hard and soft segments, and their relative contributions to overall properties can be achieved.

In one embodiment, the chemical cross-linking agent is 2-ethyl-2-(hydroxymethyl)-1,3-propanediol (also known as trimethylolpropane, as available from Sigma Aldrich Corp.), preferably from about 0 to 5 weight percent, more preferably from about 0.1 to 1 weight percent, and perhaps even more preferably from about 0.15 to 0.3 weight percent, based on the total weight of the polymer.

Additionally, and optionally, a polymer system of the present invention may contain at least one or more biocompatible catalysts that can assist in controlling the curing process, including the following periods: (1) the cure induction period, and (2) the full curing period of the biomaterial. Together these two periods, including their absolute and relative lengths, and the rate of acceleration or cure within each period, determine the cure kinetics or profile for the composition. In some embodiments, however, a catalyst is not included. For instance embodiments in which the biomaterial is heated in the course of curing, such as in a heated mold in the manner described herein, can performed without the use of a catalyst.

Some examples of suitable catalysts for preparation of the formed. PU of this invention include, but are not limited to, tin and tertiary amine compounds or combinations thereof such as dibutyl tin dilaurate (DBTDL), and tin or mixed tin catalysts including those available under the tradenames "Cotin 222", "Fomrez UL-22" (Crompton Corp.), "dabco" (a triethylene diamine from Sigma-Aldrich), stannous octanoate, trimethyl amine, and triethyl amine.

In one embodiment of the invention; the catalyst is bis-(dodecylthio)-dimethylstannane (available from Crompton Corp. as Fomrez catalyst UL-22), preferably from about 0 to 2 weight percent, more preferably from about 0 to 1 weight percent, and perhaps most preferably from 0.0009 to 0.002 weight percent, based on the total weight of the polymer.

Further, a polymer stabilizer additive useful, for protecting the polymer from oxidation may be included. In one embodiment of the invention, the additive is pentaerythritol tetrakis (3-(3,5-di-tert-butyl-4-hydroxyphenyl)proprionate (available from Ciba Specialty Chemical, Inc. as Irganox 1010), preferably from about 0 to 5 weight percent, more preferably about 0.1 to 1 weight percent, and perhaps even more preferably about 0.35 to 0.5 weight percent, based on the total weight of the polymer.

Optionally, other ingredients or additives can be included, for instance, a reactive polymer additive can be included from the group consisting of hydroxyl- or amine-terminated compounds selected from the group consisting of polybutadiene, polyisoprene, polyisobutylene, silicones, polyethylene-propylenediene, copolymers of butadiene with acryolnitrile, copolymers of butadiene with styrene, copolymers of isoprene with acrylonitrile, copolymers of isoprene with styrene, and mixtures of the above. Other additives may also be optionally provided. For example, catalysts such as Dabco, antioxidants such as vitamin E, hydrophobic additives such as hydroxyl-terminated polybutadiene, and dye green GLS, singularly or in combination, may be included in the polymer formulation.

Suitable compositions for use in the present invention are those polymeric materials that provide an optimal combination of properties relating to their manufacture, application, and in vivo use. In the uncured state, such properties include component miscibility or compatibility, processability, and the ability to be adequately sterilized or aseptically processed and stored. While the composition is curing, suitable materials exhibit an optimal combination of cure kinetics and exotherm. In the cured state, suitable compositions exhibit an optimal combination of such properties as abrasion, hardness, specific gravity, tear resistance, tensile strength, ultimate elongation, and biocompatibility.

The composition of the present invention provides a polyurethane that can be prepared ex vivo. Particularly when formed ex vivo, products incorporating the composition of this invention may be made in advance of their use, on a commercial scale, and under stringent conditions.

Polymeric biomaterials of this invention, including preferred polyurethanes can be prepared using automated manufacturing processes within the skill of those in the art. A preferred manufacturing method, for instance, includes the use of multichannel dispensing equipment to inject the polymer. Such equipment is well suited to high precision applications, having a variable or fixed number of channels, some have all channels dispensing the same volume while in others the volume can be set by channel, some have all channels dispensing the same fluid, while others allow for different fluids in different channels. The dispensing can be automated repetitive or manual. Suitable devices for metering, mixing and dispensing materials such as urethanes are commercially available from a variety of sources, including for instance from Adhesive Systems Technology Corp., 9000 Science Center Drive; New Hope, Minn. 55428.

Furthermore, polymeric biomaterials of this invention may be cured in a heated mild. The mold may receive the contents of the polymeric biomaterial before it is cured. In one embodiment, a permanent enclosed mold is used to form at least a part of the implant. Such a mold may be similar to a standard injection mold and have the ability to withstand large clamping forces. Further, such a mold may include runners and/or vents to allow material to enter and air to exit. Such a mold may be constructed from metals, polymers, ceramics, and/or other suitable materials. The mold may be capable of applying and controlling heat to the biomaterial to accelerate curing time. In some embodiments, the mold may be coated with a release coating agent to facilitate ease of removal of the cured biomaterial from the mold. Examples of suitable release agents include Teflon,™ silicone, florinated ethylene propylene (FEP), dichronite, gold, and nickel-Teflon combinations, various types of which are commercially available from a variety of sources, e.g., McLube Division of McGee Industries. In addition, the mold may be provided in two separable parts to further facilitate removal of the cured biomaterial.

Further, time and temperature parameters can be modified in processing to change the characteristics of the implant. A time temperature profile may be selected to achieve certain implant properties. In embodiments formed with a heated mold as described above, those skilled in the art will appreciate the manner in which both the temperature of the mold as well as the time biomaterial is maintained can be adjusted to change the characteristics of the molded implant.

In the embodiment in which an ex vivo curing polymer is used, the present invention preferably provides a biomaterial in the form of a curable polyurethane composition comprising a plurality of parts capable of being at least partially mixed at a time before use, the parts including: (1) a polymer component comprising the reaction product of one or more polyols, and one or more diisocyanates, and (2) a curative component comprising one or more chain extenders, one or more catalysts, and optionally, one or more polyols and/or other optional ingredients.

In some embodiments, long term congruence of the biomaterial is facilitated by its hydration in vivo, permitting the biomaterial to become more pliable, and in turn, facilitate congruence with the tibial plateau. In turn, an increase in hydration and/or changes in temperature can improve the fit and mechanical lock between the implant and the tibial plateau. The biomaterial may be hydrated ex vivo and/or in vivo, both before and after the composition is cured. Preferably, the biomaterial may be further hydrated within the joint site after the composition in order to enhance both conformance and performance of the implant.

Implantable compositions of this invention demonstrate an optimal combination of properties, particularly in terms of their physical/mechanical properties, and biocompatibility. Such performance can be evaluated using procedures commonly accepted for the evaluation of natural tissue, as well as the evaluation of materials and polymers in general, in particular, a preferred composition, in its cured form, exhibits physical and mechanical properties that approximate or exceed those of the natural tissue it is intended to provide or replace. Fully cured polymeric (e.g., polyurethane) biomaterials within the scope of this invention provide an optimal combination of such properties as abrasion, compressive hardness, compressive modulus hardness, specific gravity, tear resistance, tensile strength, ultimate elongation, tensile modulus, and biocompatibility.

Physical/Mechanical Properties and Test Methods

Various properties of the composition of this invention can be evaluated for use in quality control, for predicting service performance, to generate design data, to determine compliance with established standards, and on occasion, to investigate failures. See, for instance, Handbook of Polymer Testing: Physical Methods, edited by Roger Brown, Marcel Dekker, Inc., New York, N.Y. (1999), the disclosure of which is incorporated herein by reference. Suitable properties include those dealing with a) mass, density and dimensions, b) processability, c) strength and stiffness (including compressive hardness, compressive modulus; tensile stress-strain, flexural stress-strain, flexibility, and tear tests), c) fatigue and wear (including abrasion resistance and hardness), d) time dependent properties (such as creep, stress relaxation, compression set, tension set), e) effect of temperature (such as thermal expansion, shrinkage, and thermal oxidative aging), f) environmental resistance, and g) and biocompatibility parameters.

Of particular note are those properties that lend themselves to the preparation, delivery and long term use of improved implants having an articulating surface, and preferably for long term weight bearing use.

The preferred property ranges given below are only relevant to certain embodiments of the invention, it will be appreciated by those reasonably skilled in the art that materials having one or more properties outside the scope of the preferred ranges given below are suitable for use with the present invention.

Abrasion values for a polymer can be determined with a rotating cylindrical drum device, known as a DIN abrader. A loaded cylindrical test piece is traversed along an abrasive cloth attached to a rotating drum, and the mass loss is measured after a specified length of travel. Advantages of this device include the use of a test piece small enough to be cut from a product or a comparatively thin sheet and a much reduced risk of abrasive contamination caused by debris or smearing. The result can be expressed with the abrasion resistance index, which is the ratio of the volume loss of a black standard rubber sample to the volume loss of the test sample.

The polymer preferably provides a DIN abrasion value of less than about 70 mm$^3$, more preferably less than about 60 mm$^3$ and most preferably less than about 50 mm$^3$, as determined by ASTM Test Method D5963-96 ("Standard Test Method for Rubber Property Abrasion Resistance Rotary Drum Abrader"). DIN abrasion values of greater than about 70 mm$^3$ tend to exhibit wear rates that are too great for longer term use as articulating surface.

Biomaterial can be formed into standardized (e.g., puck-like) implant shapes and subjected to conditions intended to replicate, while also meet and exceed physiological conditions. Preferred biomaterials of this invention are able to withstand one million cycles (approximately equivalent to 1 year implantation), and more preferably greater than 5 million cycles (approximately equivalent to 5 years) before generating unsuitable debris.

Flexural stress/strain fatigue can be measured in a variety of ways. Using the standardized shape as described above, samples can be compressively loaded in cycles of increasing loads, and the stress strain fatigue can be plotted verses the number of cycles.

As another example, flexural stress/strain fatigue can be determined by a three point bending test, in which a standardized implant sample shape is supported at its anterior and posterior ends. A cyclical load is applied to the sample in an area substantially between the two supports to provide a deflection of approximately 4 mm, and the total number of cycles until failure is recorded.

Biomaterials formed into implant shapes in accordance with the present invention, under conditions intended to meet and exceed physiological conditions, are preferably able to withstand one million cycles (approximately equivalent to 1 year implantation), and more preferably greater than five million cycles (approximately equivalent to 5 years implantation) in a test similar to the one described above.

Fracture toughness can generally be determined by a number of methods. For example, fracture toughness can be measured by tests similar to ASTM Test Method D5045-99.

Preferably, the polymer provides a peak load fracture toughness of at least about 50 lbs, more preferably more than about 80 lbs, and most preferably more than about 110 lbs. Further, the polymer preferably provides an energy to break fracture toughness of greater than about 15 lb-in, more preferably greater than about 25 lb-in, and most preferably greater than about 30 lb-in. These values may be obtained with tests similar to ASTM Test Method D5045-99.

The term hardness has been applied to scratch resistance and to rebound resilience, but for polymers it is taken to refer to a measure of resistance to indentation. The mode of deformation under an indentor is a mixture of tension, shear, and compression. The indenting force is usually applied in one of the following ways: Application of a constant force, the resultant indentation being measured, measurement of the force required to produce a constant indentation, or use of a spring resulting in variation of the indenting force with depth of indentation.

A biomaterial of this invention preferably provides a hardness value when hydrated of less than about 75 Shore D, more preferably less than about 70 Shore D, and most preferably less than about 60 Shore D, as determined by ASTM Test Method D2240. In some embodiments, hydration of the biomaterial may lower the shore hardness value.

In one method of determining specific gravity, a test piece is provided weighing a minimum of 2.5 grams, which can be of any shape as long as the surfaces are smooth and there are no crevices to trap air. The test piece is weighed in air and then in water using a balance accurate to 1 mg. The test piece can be suspended by means of a very fine filament, the weight of which can be included in the zero adjustment of the balance and its volume in water ignored. The specific gravity is calculated from the difference in measurements.

The polymer preferably provides a specific gravity of about 1 to 2 $g/cm^3$, more preferably about 1 to 1.5 $g/cm^3$, and most preferably about 1.15 to 1.17 $g/cm^3$, as determined by ASTM Test Method D792.

A tear test may be used to measure tear strength. In a tear test, the force is not applied evenly but is concentrated on a deliberate flaw or sharp discontinuity in the sample and the force to produce continuously new surface is measured. This force to start or maintain tearing will depend in a complex manner on the geometry of the test piece and the nature of the discontinuity.

Preferably, a biomaterial of this invention provides a tear strength value in the Die C configuration of greater than about 400 pounds per linear inch (PLI), more preferably greater than about 600 PLI, and most preferably greater than about 800 PLI, and a value in the Die T configuration of preferably greater than about 100 PLI, more preferably greater than about 150 PLI, and most preferably greater than about 250 PLI, as determined by ASTM Test Method D624.

To measure tensile modulus, tensile strength, and ultimate elongation, a test piece of the material is stretched until it breaks, and the force and elongation at various stages is measured. A tensile machine is used to perform this test. Generally, the basic elements of a tensile machine are grips to hold the test piece, a means of applying a strain (or stress), a force-measuring instrument, and an extensometer.

The polymer preferably provides a tensile modulus at 100% elongation value of about 1,000 to 10,000 psi, more preferably about 2,000 to 5,000 psi, and most preferably about 2,500 to 4,500 psi, as determined by ASTM Test method D412.

The polymer preferably provides a tensile modulus at 200% elongation value of about 1,000 to 10,000 psi, more preferably about 2,000 to 6,000 psi, and most preferably about 2,500 to 5,000 psi, as determined by ASTM Test method D412.

The polymer preferably provides a tensile strength value of greater than about 6,000 psi, more preferably greater than about 6,500 psi, and most preferably greater than about 7,000 psi., as determined by ASTM Test Method D412.

Preferably, the polymer provides an ultimate elongation of greater than about 200%, more preferably greater than about 250%, and most preferably greater than about 300%, as determined by ASTM Test Method D412.

To measure compressive modulus and compressive strength, a sample is again formed in a standardized (e.g., puck) shape and varying compressive loads are applied to the sample in order to develop a corresponding curve. The compressive modulus can be determined from this curve. Compressive strength may be determined by applying increasing loads to a sample until the sample fails.

Preferably, the sample implant provides an compressive modulus of greater than about 4,000 psi, more preferably greater than about 4,500 psi, and most preferably greater than about 5,000 psi, as determined in the manner described above.

Preferably, the sample implant also provides a compressive strength of greater than about 6,000 psi, more preferably greater than about 7,000 psi, and most preferably greater than about 8,000 psi, as determined by a test similar to the one described above.

Water absorption may be determined in a variety of ways. A suitable method for measuring water absorption is to submerge a sample of the test material, with an implant-type geometry, in a saline solution. Once the sample and saline solution reach equilibrium at 37 degrees Celsius, which may take a month or longer, the sample is removed and weighed to determine its water absorption.

Preferably, the polymer provides a water absorption value less than about 5% at 37 C, more preferably less than about 3% at 37 C, and most preferably less than about 2% at 37 C, as determined by a test similar to the one described above.

The medical-grade polyurethane resins were evaluated for biocompatibility in accordance with ISO 10993: Biological Evaluation of Medical Devices and FDA G95-1: Required Biocompatibility Training and Toxicology Profiles for Evaluation of Medical Devices. The biological effects of the resin, such as cytotoxicity, sensitization, genotoxicity, implantation, chronic toxicity, and carcinogenicity, were studied. The tests were conducted in accordance with the FDA Good Laboratory Practice (GLP) Regulation.

The following tests were conducted to determine if the polymer is biocompatible: 1) ISO MEM elution using L-929 mouse fibroblast cells; 2) ISO agarose overlay using L-929 mouse fibroblast cells; 3) ISO acute systemic injection test; 4) ISO intracutaneous reactivity test; 5) ISO guinea pig maximization sensitization test; 6) Material mediated rabbit pyrogen test; 7) in vitro genotoxicology test; and 8) ISO muscle implantation study in the rabbit with histology-1 week. The results of the eight selected screening biocompatibility tests above show that the polymer passes all the tests and is considered biocompatible.

In an alternative embodiment, the implant can be provided by any of a series of metals, including titanium, stainless steel, cobalt chrome millithium alloys and tantalum. Other surface materials can include various ceramics and biologic polymers.

Numerous characteristics and advantages of the invention covered by this document have been set forth in the foregoing description. It will be understood, however, that this disclosure is, in many respects, only illustrative. Changes can be made in details, particularly in matters of shape, size and ordering of steps without exceeding the scope of the invention. The invention's scope is, of course; defined in the language in which the appended claims are expressed.

What is claimed is:

1. A monolithic tibiotalar implant for use in arthroplasty repair of ginglymus joints, comprising: a first major surface of the monolithic implant curved for positioning against a tibia and configured to allow the tibia to articulate across the first major surface; a second major surface of the monolithic implant curved for positioning against a talus; and a protrusion proximate to the implant's anterior side sized to engage the neck of the talus, wherein the first and second major surfaces curve only in an anterior-posterior direction, and wherein the first major surface is curved differently than the second major surface such that the first major surface is adapted to be congruent with the tibia and the second major surface is adapted to be congruent with the talus, and wherein the monolithic implant is comprised of a polymeric biomaterial that includes both hard and soft segments to provide at least one of desirable wear resistance, congruency, and cushioning properties.

2. The implant according to claim 1 wherein the monolithic tibiotalar implant has one or more external structures adapted to improve retention of the implant within the joint site.

3. The implant according to claim 2 wherein the protrusion is located on the implant's anterior side.

4. The implant according to claim 1 wherein the implant is comprised of a biomaterial.

5. The implant according to claim 4 wherein the biomaterial is a polyurethane.

6. The implant according to claim 5 wherein the polyurethane is biocompatible with respect to cytotoxicity, sensitization, genotoxicity, chronic toxicity, and carcinogenicity.

7. The implant according to claim 5 wherein the polyurethane has a Shore hardness of at least about 60 D or less.

8. A method of repairing a tibiotalar joint, comprising the steps of providing and implanting an implant according to claim 1, the implant being inserted through an incision anterior to the tibiotalar joint.

9. The implant according to claim 1 inserted into a ginglymus joint, the ginglymus joint being a tibiotalar joint, the monolithic implant's first major surface positioned against the tibia, its second major surface positioned against the talus, and the protrusion proximate the implant's anterior side is engaged with a neck of the talus.

10. The implant according to claim 1, wherein the implant is made of polyurethane having hard and soft segments.

11. The implant according to claim 10, wherein the hard segments are made of oligourethane units formed from diisocyanate and chain extender, and wherein the soft segments are made of polyol units.

12. A monolithic device for implantation into an ankle joint space within the body of a mammal, the device comprising:
a monolithic structure fabricated from a biocompatible, biodurable material that is configured to be inserted into the joint compartment, the monolithic structure including first and second major surfaces, the first major surface curved for positioning against a tibia, such that the tibia can articulate across the first major surface, and the second major surface curved for positioning against a talus, wherein the monolithic device is substantially free of anchoring portions that need to be attached to the bone, cartilage, ligaments or other tissue, wherein the first and second major surfaces curve only in an anterior-posterior direction, and wherein the first major surface is curved differently than the second major surface such that the first major surface is adapted to be congruent with the tibia and the second major surface is adapted to be congruent with the talus, and wherein the monolithic implant is comprised of a polymeric biomaterial that includes both hard and soft segments to provide at least one of desirable wear resistance, congruency, and cushioning properties.

13. The device according to claim 12 wherein stability of the device within the joint space is provided by the congruency of the device to the talus.

14. The device according to claim 12, wherein the monolithic structure is made of polyurethane having hard and soft segments.

15. The device according to claim 14, wherein the hard segments are made of oligourethane units formed from diisocyanate and chain extender, and the soft segments are made of polyol units.

16. A monolithic interpositional tibiotalar implant for use in repairing joints of the ankle, comprising:
a first major surface curved for positioning against a tibia and curved to allow the tibia to articulate across the first major surface; and
a second major surface curved for positioning against a talus, wherein the implant has a protrusion proximate its anterior side configured to engage the neck of a talus to improve fixation to the talus,
wherein the monolithic implant is comprised of a polymeric biomaterial that includes both hard and soft segments to provide at least one of desirable wear resistance, congruency, and cushioning properties, and
wherein the first and second major surfaces curve only in an anterior-posterior direction.

17. The implant according to claim 16, wherein the hard segments are made of oligourethane units formed from diisocyanate and chain extender, and wherein the soft segments are made of polyol units.

* * * * *